United States Patent [19]  [11] 3,998,734
Barringer  [45] Dec. 21, 1976

[54] METHOD AND APPARATUS FOR TRANSFERRING PARTICLES FROM ONE FLUID STREAM INTO ANOTHER

[75] Inventor: Anthony Rene Barringer, Willowdale, Canada

[73] Assignee: Barringer Research Limited, Rexdale, Canada

[22] Filed: Jan. 8, 1973

[21] Appl. No.: 321,852

[30] Foreign Application Priority Data
Jan. 12, 1972 Canada .............................. 132220

[52] U.S. Cl. .................................... 210/65; 73/28; 55/17
[51] Int. Cl.² ................. B01D 45/04; G01N 31/00
[58] Field of Search ..................... 210/65; 209/210; 137/808, 809; 73/28; 55/17, 277

[56] References Cited
UNITED STATES PATENTS

| 3,091,334 | 4/1963 | Morton | 209/210 |
| 3,208,463 | 9/1965 | Hurvitz | 137/808 |
| 3,405,736 | 10/1968 | Reader et al. | 137/842 |
| 3,458,237 | 7/1969 | Noe | 137/809 |

Primary Examiner—Charles N. Hart
Assistant Examiner—Ferris H. Lander
Attorney, Agent, or Firm—Rogers, Bereskin & Parr

[57] ABSTRACT

Particles in a first fluid are transferred to a second fluid by confronting a stream of the first fluid with a stream of the second fluid in an enclosed region so that the particles will travel from the first fluid across said region to the second fluid by virtue of their momentum. The respective pressures of the first and second fluids is such that there is no appreciable mixing of the stream of the second fluid carrying particles with the first fluid.

1 Claim, 5 Drawing Figures

METHOD AND APPARATUS FOR TRANSFERRING PARTICLES FROM ONE FLUID STREAM INTO ANOTHER

This invention relates to a method and an apparatus for transferring particulate matter carried in a fluid stream which may be a gas or liquid into another fluid stream which may also be a gas or liquid. It is of particular application in carrying out chemical analyses of particulates. In the field of air pollution studies and geochemical investigation of atmospheric particulate dispersions, it is sometimes required to analyze the particulates in the atmosphere on a continuous basis. In such cases it is useful to transfer these particulates from suspension in air to suspension in a gas or liquid stream.

Figure 1:
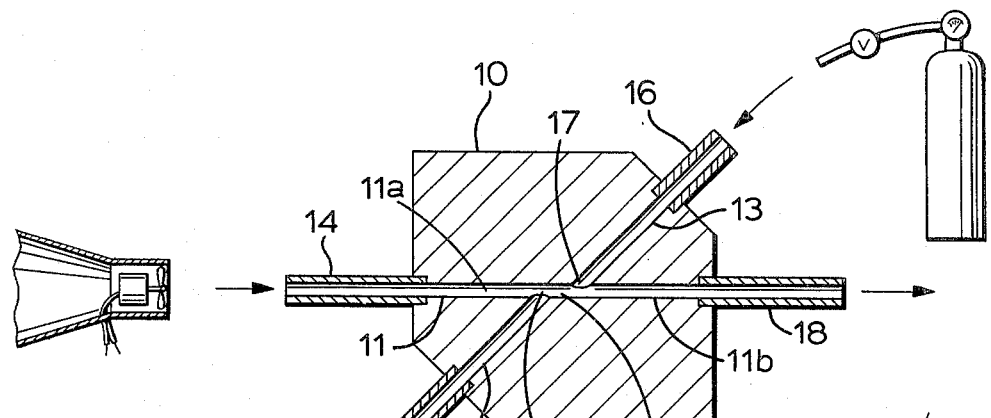
Figure 2:
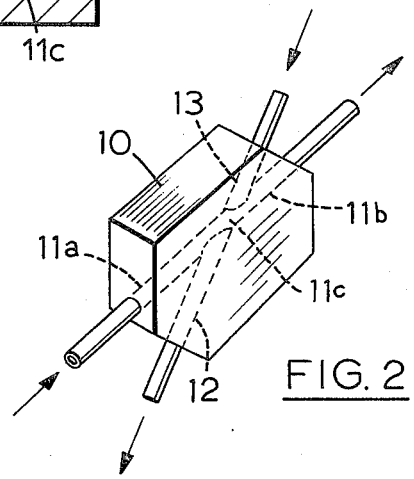
Figure 3:
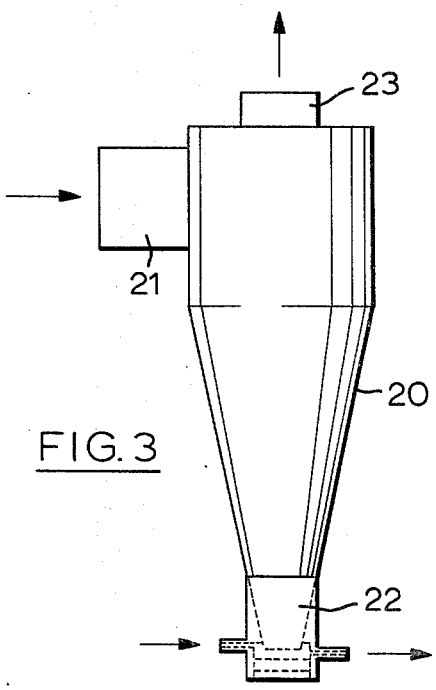
Figure 5:
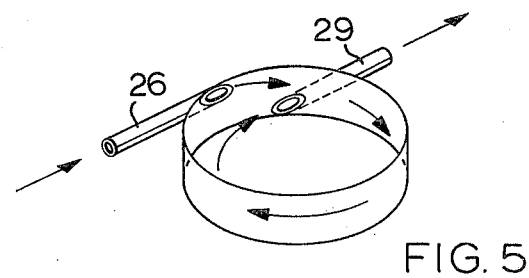
Figure 4:
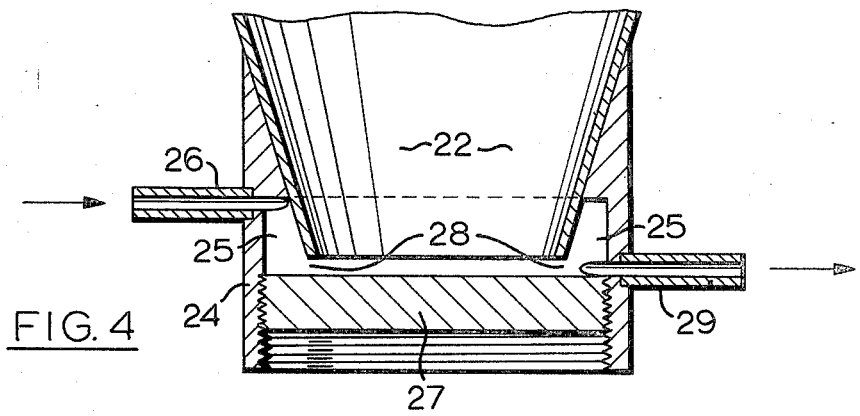

This may be achieved according to the invention by accelerating the particles in their supporting air carrier to a high velocity and then separating and projecting said particles from the fast moving air stream into a collecting stream of gas or liquid. The collecting stream confronts the air stream in an enclosed region, and the respective pressures of the two streams is such that the collecting stream laden with particulates is substantially free of air. The particles are transferred across the interface between the air stream and the collecting stream in the enclosed region by virtue of their momentum.

In the drawings,

FIG. 1 is a sectional view of a preferred form of a transfer block according to the invention, FIG. 2 is a perspective view of the transfer block shown in FIG. 1, FIG. 3 is a somewhat diagrammatic side view of an alternative embodiment of the invention, FIG. 4 is a side sectional view, partly broken away, showing the lower end of the embodiment shown in FIG. 3, and FIG. 5 is a diagrammatic perspective view showing the direction of the collecting stream in the embodiment of FIGS. 3 and 4.

Referring to FIGS. 1 and 2, a preferred embodiment of the invention includes a block 10 (e.g. of metal) in which three holes 11, 12 and 13 have been drilled. Portion 11*a* of the hole 11 and the hole 12 constitute a first fluid receiving means, which may be connected through inlet 14 of the hole 11*a* to a pressurized souce of source first fluid, e.g. air containing particulates. The portion 11*a* of the hole 11 constitutes a first channel and it is connected to the hole 12 (which constitutes a second channel) at a first junction 15. Similarly, the hole 13 and portion 11*b* of the hole 11 constitute a second fluid receiving means which may be connected through inlet 16 of the hole 13 to a source of a second fluid under pressure, e.g. an inert gas such as argon, helium, etc. The hole 13 constitutes a third channel and the hole 11*b* constitutes a fourth channel, the former being connected to the latter at a second junction 17. Portion 11*c* of the hole 11 which is located between the first and second junctions 15 and 17 constitutes an enclosed reservoir in which the opposing fluid streams meet, as will be explained.

For the purpose of the following discussion it will be assumed that the first fluid is air and the second fluid is an inert gas. Air containing particulates is formed into a stream by any conventional means, e.g. a blower or a ram intake duct on a moving vehicle. The velocity of the air may vary widely, e.g. between a few inches per second to several hundred feet per second. The inert gas is delivered to the block 10 from a pressurized source of adjustable flow rate. The air stream meets the inert gas stream in the enclosed region 11*c*, and the respective pressures of the two streams is precisely balanced so that the air stream is forced to turn back or at least partially reverse its direction and exit through the hole 12. Likewise, the inert gas stream is forced to turn back and exit through outlet 18 of the hole 11*b*. Under these conditions the particles carried in the air stream continue in a straight path through the region 11*c* and are transferred by virtue of their inertia and momentum into the inert gas stream. If the particles are relatively large, for example in the 50–200 micron diameter region, the transfer process can take place at relatively low velocities of a few inches per second due to the mass of the particles. If the particles are small, however, for example in the one micron diameter range, it is desirable to use higher velocities of several tens of feet per second in order to impart sufficient momentum to the particles so that they will readily transfer and will not be entrained in the air stream and swept out through the hole 12.

Whereas the invention has been described as being applicable to particles carried in a gaseous stream it will be noted that it is equally applicable to particles carried in a liquid stream providing the specific gravity of the particles is significantly higher than that of the liquid. Thus, for example, a stream of silicate particles having a specific gravity of 2.4 may be carried in a stream of an aqueous fluid having a specific gravity of 1 into the hole 11*a*. Another aqueous stream may be brought in through hole 13 where it will meet the first stream in the region 11*c*. Providing that the streams have equal pressure and are moving at relatively high velocity, the particles carried in the first stream will be projected in a straight line into the second stream. The first stream will be ejected through hole 12 and the particles will be transferred to the second stream and exit through the hole 11*b*.

Any combination of liquids or gas can be used in the device including transfer from gas to liquid, gas to gas, liquid to liquid or liquid to gas. In practice it is desirable to keep the pressure of the second fluid entering through the hole 13 slightly in excess of the first fluid entering through the hole 11*a*. Under these conditions there will be a slight loss of the second fluid exiting through the hole 12 but particulate transfer will still take place. A slight excess of pressure ensures that there is no contamination of the second fluid exiting through the hole 11*b* by the first fluid. This condition ensures a virtually perfect tranfer since the particles are washed by a slight counter current of excess second fluid in the vicinity of the region 11*c*.

The invention as described above has referred to the use of linear motion, however, the invention is equally applicable to circular motion. An embodiment of the invention employing circular motion is shown in FIGS. 3, 4 and 5. A miniature cyclone 20 of conventional design may be employed. Air or other fluid containing particulates enters into the cyclone at inlet 21 and a vortex is created inside the cyclone in the well known manner of operation of cyclones such that the particulates move towards the base 22 of the cyclone 20 with a high speed circular motion. Clean fluid devoid of particulates is ejected from the cyclone at outlet 23. A housing 24 is attached to the base of the cyclone 20 as illustrated at larger scale in FIG. 4, and it provides an annular chamber 25 which surrounds the base 22 of the cyclone 20. In the housing 24 a stream of fluid to which it is desired to transfer the particulates enters through a side tube 26. The fluid flow creates a vortex inside the annular chamber 25. The annular chamber 25 has a wall 27 that is separated from the adjacent end of the cyclone base 22 by a gap 28 of adjustable height. The vortex formed in the annular chamber 25 is arranged to be in the same direction as the vortex inside the cyclone. This vortex is achieved by offsetting the entrance and exit tubes as shown in FIG. 5.

In operation, particles moving down the walls of the cyclone are ejected through the gap 28 in a radial direction due to the large centrifugal force on these particles. They are flung outwards into the annular chamber 25 where they are picked up by the vortex formed by the fluid entering through the side tube 26. The particles are spun around in a vortex formed inside the annular chamber 25 and are ejected through an exit tube 29.

It is important to maintain the pressure of fluid entering through the side tube 26 at a slightly higher pressure than the pressure existing in the base of the cyclone. Under these conditions there is a slight counter current of fluid through the gap 28 into the base of the cyclone where it is entrained in the air or other carrier fluid being exhausted from the cyclone. The particles by virtue of their high centrifugal force are ejected with considerable velocity against the slight incoming flow of fluid.

Applications of the invention that have been described refer to its use for analytical purposes. However, it will be appreciated that it can also be used as a convenient method of continuously clearing dust from the base of a cyclone and injecting the dust into a concentrated stream of water or air so that it can be piped to a convenient collection point.

What I claim is:

1. A method of transferring particles contained in a first fluid into a second fluid, said particles having a higher specific gravity than the specific gravity of said first fluid, said method comprising the steps of moving said first fluid and the particles therein contained in a first predetermined direction, moving said second fluid in a second predetermined direction, directing said second fluid and said first fluid into a common region, setting the pressure of supply of said second fluid to the common region greater than the pressure of supply of said first fluid to said region such that the first fluid is constrained to flow at all times out of a first predetermined exit of the said common region, a first portion of the second fluid flows out of a second predetermined exit of the common region free of the first fluid, and the remainder of the second fluid flows out of the said first predetermined exit, and such that the said particles in said first fluid are transferred across said region to said first portion of the second fluid by virtue of their momentum.

* * * * *